US011622999B2

(12) United States Patent
Fischetti et al.

(10) Patent No.: US 11,622,999 B2
(45) Date of Patent: Apr. 11, 2023

(54) COMPOSITIONS AND METHODS COMPRISING LYSIN PLYCP025 AND DERIVATIVES THEREOF (71) Applicant: The Rockefeller University, New York, NY (US)

(72) Inventors: Vincent Fischetti, West Hempstead, NY (US); Qiong Wang, New York, NY (US)

(73) Assignee: The Rockefeller University, New York, NY (US)

(*) Notice: Subject to any disclaimer, the term of this patent is extended or adjusted under 35 U.S.C. 154(b) by 234 days.

(21) Appl. No.: 16/772,048

(22) PCT Filed: Dec. 11, 2018

(86) PCT No.: PCT/US2018/065016
§ 371 (c)(1),
(2) Date: Jun. 11, 2020

(87) PCT Pub. No.: WO2019/118506
PCT Pub. Date: Jun. 20, 2019

(65) Prior Publication Data
US 2021/0169995 A1 Jun. 10, 2021

Related U.S. Application Data (60) Provisional application No. 62/598,039, filed on Dec. 13, 2017.

(51) Int. Cl.
A61K 38/47 (2006.01)
C12N 15/63 (2006.01)

(52) U.S. Cl.
CPC .............. A61K 38/47 (2013.01); C12N 15/63 (2013.01); C12Y 302/01017 (2013.01)

(58) Field of Classification Search
None
See application file for complete search history.

(56) References Cited

U.S. PATENT DOCUMENTS 8,962,297 B2    2/2015  Seal et al.
2005/0153415 A1 7/2005  Zimmer et al.
2016/0017307 A1 1/2016  Mayer

FOREIGN PATENT DOCUMENTS

WO    2020157519 A1    8/2020

OTHER PUBLICATIONS

NCBI information for WP_025647622, Retrieved from < https://www.ncbi.nlm.nih.gov/protein/WP_025647622.1/ > on May 27, 2022.*
Simmons, M., et al., Recombinant Expression of Two Bacteriophage Proteins That Lyse Clostridium perfringens and Share Identical Sequences in the C-Terminal Cell Wall Binding Domain of the Molecules but Are Dissimilar in Their N-Terminal Active Domains, Journal of Agricultural and food Chemistry, Sep. 8, 2010, vol. 58, Issue 19, pp. 10330-10337.
Tillman, G.E., et al., Expression of a Clostridium perfringens genome-encoded putative N-acetylmuramoyl-L-alanine amidase as a potential antimicrobial to control the bacterium, Archives of Microbiology, Aug. 11, 2013, vol. 195, Issue 10, pp. 675-681.
Swift, S.M., et al., A Thermophilic Phage Endolysin Fusion to a Clostridium perfringens-Specific Cell Wall Binding Domain Creates an Anti-Clostridium Antimicrobial with Improved Thermostability, Viruses, Jun. 12, 2015, vol. 7, Issue 6, pp. 3019-3034.
Anonymous, UniParc sequence UPI0003F8E66C, Aug. 27, 2015, 1 page. https://www.uniprot.org/uniparc/UPI0003F8E66C.
UniProtKB accession No. A0A1I7J8I4_9CLOT, Nov. 22, 2017, 1 page. https://www.uniprot.org/uniprot/A0A1I7J8I4.

* cited by examiner

Primary Examiner — Suzanne M Noakes
(74) Attorney, Agent, or Firm — Hodgson Russ LLP (57) ABSTRACT Provided are compositions and methods for use in selectively killing one or more of *C. perfringens, C. sordelli* and *C. histolyticum*. The compositions include lysin PlyCP025, as well as catalytically active fragments thereof, and variants thereof that retain killing activity. Methods for reducing one or more of *C. perfringens, C. sordelli* or *C. histolyticum* bacteria are provide and involve contacting such bacteria with a composition that contains PlyCP025 or an enzymatically active fragment or variant thereof, which can be provided as recombinant polypeptides. The composition and methods are useful for human and veterinary purposes. Diagnostic approaches are also included by contacting a sample obtained or derived from an animal, with a recombinant polypeptide, and detecting binding of the polypeptide to bacteria in the sample if said bacteria that are bound to the polypeptide are present in the sample. The polypeptide may thus be detectably labeled to produce a detectable signal.

14 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 229
<212> TYPE: PRT
<213> ORGANISM: Clostridium perfringens

<400> SEQUENCE: 1

Met Ser Lys Ile Phe Gly Leu Asp Ala Gly His Cys Thr Ser Gly Ala
1               5                   10                  15

Asp Thr Gly Ala Gln Gly Asn Gly Tyr Lys Glu Gln Asp Leu Thr Arg
            20                  25                  30

Gln Val Val Thr Tyr Leu Ser Glu Tyr Leu Glu Lys Glu Gly His Thr
        35                  40                  45

Thr Lys Tyr Cys His Cys Asn Ser Ala Ser Thr Val Asn Glu Ser Leu
    50                  55                  60

Arg Tyr Arg Val Asn Lys Ala Asn Ser Ile Gly Val Asp Tyr Phe Val
65                  70                  75                  80

Ser Ile His Leu Asn Ala Gly Gly Gly Val Gly Thr Glu Thr Tyr Ile
                85                  90                  95

Cys Ala Arg Gly Gly Glu Ala Glu Arg Val Ala Lys Arg Val Asn Ser
            100                 105                 110
```

Lys Leu Val Gln Tyr Gly Tyr Arg Asp Arg Gly Val Lys Val Gly Asn
            115                 120                 125

Leu Tyr Val Ile Lys Asn Thr Asn Ala Pro Ala Ile Leu Val Glu Ile
        130                 135                 140

Cys Phe Ile Asp Ser Ser Ser Asp Val Ala Lys Phe Asn Ala Lys Ala
145                 150                 155                 160

Ile Ala Lys Ala Ile Ala Glu Gly Leu Leu Asp Lys Thr Ile Gly Glu
                165                 170                 175

Val Glu Asn Lys Pro Glu Ser Val Pro Ser Asn Thr Glu Thr Ser Asn
            180                 185                 190

Thr Tyr Phe Arg Val Val Gly Ser Tyr Lys Asp Arg Glu Asn Ala
        195                 200                 205

Val Lys Lys Gln Glu Glu Leu Lys Ala Lys Gly Glu Asp Ser Phe Leu
    210                 215                 220

Leu Ala Tyr Lys Glu
225

<210> SEQ ID NO 2
<211> LENGTH: 175
<212> TYPE: PRT
<213> ORGANISM: Clostridium perfringens

<400> SEQUENCE: 2

Met Ser Lys Ile Phe Gly Leu Asp Ala Gly His Cys Thr Ser Gly Ala
1               5                   10                  15

Asp Thr Gly Ala Gln Gly Asn Gly Tyr Lys Glu Gln Asp Leu Thr Arg
            20                  25                  30

Gln Val Val Thr Tyr Leu Ser Glu Tyr Leu Glu Lys Glu Gly His Thr
        35                  40                  45

Thr Lys Tyr Cys His Cys Asn Ser Ala Ser Thr Val Asn Glu Ser Leu
    50                  55                  60

Arg Tyr Arg Val Asn Lys Ala Asn Ser Ile Gly Val Asp Tyr Phe Val
65                  70                  75                  80

Ser Ile His Leu Asn Ala Gly Gly Gly Val Gly Thr Glu Thr Tyr Ile
                85                  90                  95

Cys Ala Arg Gly Gly Glu Ala Glu Arg Val Ala Lys Arg Val Asn Ser
            100                 105                 110

Lys Leu Val Gln Tyr Gly Tyr Arg Asp Arg Gly Val Lys Val Gly Asn
            115                 120                 125

Leu Tyr Val Ile Lys Asn Thr Asn Ala Pro Ala Ile Leu Val Glu Ile
        130                 135                 140

Cys Phe Ile Asp Ser Ser Ser Asp Val Ala Lys Phe Asn Ala Lys Ala
145                 150                 155                 160

Ile Ala Lys Ala Ile Ala Glu Gly Leu Leu Asp Lys Thr Ile Gly
                165                 170                 175

<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
gccgccgaat tcattatgag caaaatcttt ggtctggatg c         41

```
<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
ggcttccaga cgacctgttt tggtagccga ttgacgtccg c          41
```

COMPOSITIONS AND METHODS COMPRISING LYSIN PLYCP025 AND DERIVATIVES THEREOF

CROSS REFERENCE TO RELATED APPLICATIONS

This application claims priority to U.S. Provisional Application No. 62/598,039, filed on Dec. 13, 2017, the disclosure of which is hereby incorporated by reference.

FIELD

The present disclosure relates generally to methods, compositions and articles of manufacture useful for the prophylactic and therapeutic amelioration and treatment of Gram-positive bacteria, including but not necessarily limited to *Clostridium perfringens* bacterial strains. The disclosure relates to compositions and articles of manufacture incorporating isolated and engineered *C. perfringens* bacteriophage lysins including variants and truncations thereof, and to methods utilizing the lysin polypeptides and compositions.

BACKGROUND

*Clostridium peifringens*, a Gram-positive, rod-shaped, anaerobic. spore-forming bacterium. *C. perfringens* may be found as a component of decaying vegetation and the intestinal tract of humans and other vertebrates, insects, and in the soil. *C. perfringens* can cause severe infections of animals and humans, and is known to be the cause of food poisoning, gas gangrene, necrotic enteritis, and gastrointestinal infections not associated with food. Generally, *C. perfringens* is a pathogen that affects both animals and humans. Although *C. perfringens* has been known to infect all animals it is a particularly prevalent pathogen in the poultry industry.

*C. perfringens* causes necrotic enteritis in chickens. Clinical illness is usually short lived but the mortality in poultry flocks can be high with obvious financial and animal health implications. Sometimes the only sign of necrotic enteritis is a sudden increase in mortality. However, necrotic enteritis may cause birds to appear depressed, have ruffled feathers, and dark diarrhea. The disease may persist in a flock for about 5-10 days, with up to 50% mortality.

Antimicrobial drugs delivered at prophylactic doses in water or feed may control necrotic enteritis. However, there is increasing public opposition to the use of antibiotics in animal husbandry. But without traditional antibiotics to prevent necrotic enteritis, this disease could potentially become a greater problem for the poultry industry. Thus, there is a need to identify new ways to prevent or treat infections by *C. perfringens*.

SUMMARY OF THE DISCLOSURE

The present invention provides compositions and methods for use in selectively killing certain types of bacteria. Non-limiting embodiments are implemented using a lysin referred to herein as PlyCP025, including catalytically active fragments thereof, and variants thereof that retain killing activity. In this regard, the lysin comprises a lytic enzyme segment, and thus contains a lytic polypeptide sequence that is suitable for treating and/or preventing *C. perfringens* infections, as well as infection by certain other bacteria, including but not necessarily limited to *C. sordelli* and *C. histolyticum*. However, the same polypeptides exhibits less, or no detectable activity against *C. septicum, C. bifermentans* and *C. difficile* and certain other bacteria. Thus, the compositions and methods are useful for selectively killing bacteria in a targeted manner.

In non-limiting embodiments, the disclosure includes a method for reducing one or more of *C. perfringens, C. sordelli* or *C. histolyticum* bacteria. The method generally comprises contacting the bacteria with a composition comprising a lytic enzyme described herein. In embodiments, the lytic enzyme comprises the amino acid sequence of SEQ ID NO: 2 or an amino acid sequence with a contiguous segment having at least 95% identity to the amino acid sequence of SEQ ID NO:2 such that one or more of the one or more of the *C. perfringens, C. sordelli* or *C. histolyticum* bacteria are killed. In embodiments, the lytic enzyme consists of the sequence of SEQ ID NO:2 or an amino acid sequence with a contiguous segment having at least 95% identity to the amino acid sequence of SEQ ID NO:2. In certain aspects, any one or a combination of *C. perfringens, C. sordelli* or *C. histolyticum* bacteria are killed. In embodiments, at least *C. perfringens* bacteria are killed. In embodiments, any one or any combination of the bacteria are antibiotic resistant and are killed. In embodiments, the bacteria are killed are in or on a human, or in or on a non-human animal selected from avian animals and non-human mammals. In embodiments, the bacteria are in the individual in a population of bacteria that further comprise commensal gut bacterium, but the commensal gut bacteria are not killed by the lytic enzyme. In certain approaches, the commensal bacteria are selected from *C. septicum, C. novyi, E. faecalis, E. faecium, L. rhamnosous*, and combinations thereof.

In another embodiment, the disclosure provides a pharmaceutical formulation, which may be provided as a veterinary formulation, for killing *C. perfringens, C. sordelli* or *C. histolyticum*, or a combination thereof. The formulation(s) comprise a lytic enzyme described herein, and at least one pharmaceutically acceptable carrier or excipient.

In another embodiment, the disclosure provides a method of making a recombinant polypeptide capable of killing *C. perfringens, C. sordelli* and *C. histolyticum* as described herein. This approach comprises expressing the recombinant polypeptide in a population of cells comprising an expression vector that encodes and expresses the recombinant polypeptide, allowing expression of the recombinant polypeptide, and separating the recombinant polypeptide from the population of cells. The expression vectors, and cells comprising the expression vectors are also included.

In certain aspects the disclosure comprises one or more bacteria, such as a population of bacteria, that are in physical association with a recombinant polypeptide described herein. In embodiments, such bacteria are present on a mammal, or on an avian animal.

Diagnostic approaches are also included. Diagnostic approaches comprise contacting a sample obtained or derived from an animal, such as a mammal or an avian animal, with a polypeptide described herein, and detecting binding of the polypeptide to bacteria in the sample if said bacteria that are bound to the polypeptide are present in the sample. In non-limiting examples, the polypeptide is detectably labeled, and a signal from the detectable label is detected if bacteria that are bound to the polypeptide are present in the sample.

BRIEF DESCRIPTION OF THE DRAWINGS

FIG. 2A. The effect of pH on the lytic activity of PlyCP025cat. The lytic activity was determined by OD600 reduction over 60 minutes. For each sample, 30 μg of lysin or equal volume of phosphate buffer (PB) was added to *C. perfringens* ATCC13124 resuspension (20 mM PB, pH 6, 7, and 8 respectively).

FIG. 2B. The effect of NaCl on the lytic activity of PlyCP025cat. The lytic activity determined by OD600 reduction over 60 minutes. For each sample, 30 μg of lysin or equal volume of PB is added to *C. perfringens* ATCC13124 resuspension (20 mM PB, pH 8, with the addition of 20 mM NaCl, 100 mM NaCl, 200 mM NaCl, 400 mM NaCl and 500 mM NaCl respectively).

FIG. 3. Host specificity of PlyCP025cat. The lytic activity of PlyCP025cat was assessed in a variety of bacteria species, including other clostridia and other common gut flora bacteria. The effect of PlyCP025cat is measured by calculating the OD600 ratio between 60 min and the starting value FIG. 4. Graph showing comparison of the activity of PlyCP025 and PlyCP025cat.

DETAILED DESCRIPTION

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The present invention provides compositions and methods related to a lysin referred to herein as PlyCP025. The lysin comprises a lytic enzyme and thus contains a lytic polypeptide sequence that is suitable for treating and/or preventing *C. perfringens* infections, as well as infection by certain other bacteria. In this regard, it is believed that PlyCP025 and a catalytic fragment of it exhibit effective lytic activity against *C. perfringens* strains, as well as against *C. sordelli* and *C. histolyticum*. However, the same polypeptides display little to no activity against *C. septicum, C. bifermentans* and *C. difficile*. Thus, in embodiments, a composition of this disclosure exhibits greater lytic activity against *C. perfringens* relative to any suitable reference value, including but not necessarily limited to lytic activity against one or combination of *C. septicum, C. bifermentans* and *C. difficile*. Lytic activity can be measured using any suitable approach. In embodiments, lytic activity is measured via a change in CFU.

As used herein a "lytic enzyme" and "lytic polypeptide sequence" is a bacterial cell wall lytic enzyme that kills and/or is capable of killing one or more bacteria under suitable conditions and during a relevant time period. In particular embodiments a composition of the disclosure comprises a contiguous segment or variant of the polypeptide encoded by a PlyCP025 gene, the sequence of which is provided under NCBI database (WP_025647622.1), from which the nucleotide sequence is incorporated herein by reference as it exists on the filing of this date of this application or patent. The amino acid sequence of this polypeptide is:

(SEQ ID NO: 1)
*MSKIFGLDAGHCTSGADTGAQGNGYKEQDLTRQVVTYLSE*

*YLEKEGHTTKYCHCNSASTVNESLRYRVNKANSIGVDY*

*FVSIHLNAGGGVGTETYICARGGEAERVAKRVNSKLVQY*

*GYRDRGVKVGNLYVIKNTNAPAILVEICFIDSSSDVAKF*

*NAKAIAKAIAEGLLDKTIG*EVENKPESVPSNTETSNTYFRVVVGSY

KDRENAVKKQEELKAKGEDSFLLAYKE, wherein the catalytic domain is shown in bold and italics. A polypeptide that has the sequence of SEQ ID NO:1 is referred to herein from time to time as PlyCP025.

In embodiments, the disclosure comprises a lytic polypeptide derived from PlyCP025, and thus may comprise a contiguous segment or variant of the catalytic domain of PlyCP025. The catalytic domain of PlyCP025 which is annotated above in bold and italics has the sequence:

(SEQ ID NO: 2)
MSKIFGLDAGHCTSGADTGAQGNGYKEQDLTRQVVTYLSEYLEKEGHTTKY

CHCNSASTVNESLRYRVNKANSIGVDYFVSIHLNAGGGVGTETYICARGGE

AERVAKRVNSKLVQYGYRDRGVKVGNLYVIKNTNAPAILVEICFIDSSSDV

AKFNAKAIAKAIAEGLLDKTIG, which is shown in bold an italics in the first 175 amino acids of SEQ ID NO:1. A polypeptide that is the catalytic domain of PlyCP025 is referred to herein from time to time as PlyCP025cat.

In embodiments, the present disclosure comprises polypeptides that comprise or consist of the sequence given for PlyCP025 or PlyCP025cat, or variants thereof. In embodiments, the polypeptide is capable of binding specifically to and/or lysing cells of *C. perfringens* strains, and may also be capable of lysing *C. sordelli* and *C. histolyticum*. Thus, the disclosure provides lytic polypeptides that are capable of killing such bacteria, for instance by having at least some cell wall lytic activity against the host bacteria. In certain embodiments the polypeptides may be extended to include, for example, amino acids C-terminal to amino acid 175 in SEQ ID NO:1. In embodiments, between 1-53 amino acids C-terminal to amino acid 175 in SEQ ID NO:1 can be included.

In certain implementations the disclosure includes polypeptides and methods of using them, wherein the polypeptides comprise a functionally active lytic enzyme that shares a particular percent amino acid sequence identity with SEQ ID NO:1 and/or SEQ ID NO:2, and can kill for *C. perfringens* bacteria, and other susceptible bacteria as described herein. Percent amino acid sequence identity with respect to the phage associated lytic enzyme sequences identified is defined herein as the percentage of amino acid residues in a polypeptide sequence of this disclosure that are identical with the amino acid residues in a phage associated lytic enzyme sequence, after aligning the sequences in the same reading frame and introducing gaps, if necessary, to achieve the maximum percent sequence identity, and not considering any conservative substitutions as part of the sequence identity. In embodiments, polypeptides of this disclosure have at least 60, 65, 70, 75, 80, 85, 90, 95, 97, 98, 99 or 99.5% amino acid sequence, inclusive, and including all numbers there between to the first decimal point, identity with SEQ ID NO:1 or SEQ ID NO:2. The disclosure further includes polypeptides comprising or consisting of SEQ ID NO:1 and SEQ ID NO:2 and polypeptides having the stated amino acid sequence identity, wherein one or more amino acid residues are added, or deleted, wherein such amino acid insertions or deletions may be within the polypeptide, or at the N or C terminus of the sequences.

Biologically active portions of polypeptides of this disclosure can also comprise mutations, provided such mutant proteins maintain approximately, at least as much, or exhibit more lytic activity than a polypeptide comprising or consisting of SEQ ID NO:1 or SEQ ID NO:2. Such mutants or variants thereof may have a predicted function and/or can be tested for function or the capability to kill bacteria. Thus, changes can be made to the sequence of SEQ ID NO:1 and/or SEQ ID NO:2, for example, and mutants or variants having a change in sequence can be tested using the assays and methods described and exemplified herein, and/or as will be otherwise apparent to those skilled in the art. Thus, when given the benefit of the present disclosure, a skilled artisan can predict one or more amino acids suitable for substitution or replacement and/or one or more amino acids which are not suitable for substitution or replacement, including reasonable conservative or non-conservative substitutions. Certain substitutions include but are not limited to: Lys for Arg and vice versa such that a positive charge may be maintained; Glu for Asp and vice versa such that a negative charge may be maintained; Ser for Thr such that a free hydroxide can be maintained; and Gln for Asn such that a free amine can be maintained. Exemplary conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (K) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa. Amino acid substitutions are typically of single residues, or can be of one or more, one or a few, one, two, three, four, five, six or seven residues; insertions usually will be on the order of about from 1 to 10 amino acid residues; and deletions will range about from 1 to 30 residues. Deletions or insertions may be in single form, but typically are made in adjacent pairs, i.e., a deletion of 2 residues or insertion of 2 residues.

When used according to methods of this disclosure, PlyCP025 and variants thereof (including but not limited to PlyCP025cat) may be used as exogenous agents that are uncoupled from a requirement for intracellular expression, and are accordingly suitable for use in pharmaceutical formulations that are described more fully below. Accordingly, in certain aspects, the disclosure provides a single bacterium, and populations of bacteria that are in physical association with polypeptides of this disclosure. In certain embodiments, the disclosure comprises a population of *C. perfringens*, and optionally *C. sordellii* and *B. subtilis* and combinations thereof, wherein the bacterial cells comprise a polypeptide of this disclosure in physical association with a component of peptidoglycan present in the bacteria. In embodiments, the peptidoglycan may comprise N-deacylated glucosamine (N-deacylated NAG), N-acetylmuramic acid (NAM), N-deacylated NAM, or any combinations thereof. In one embodiment, the peptidoglycan structure is comprised of alternating NAM and NAG residues, which may be N-deacetylated, and where a tripeptide, tetrapeptide, or pentapeptide bound to the NAM residues, is crosslinked between the third amino acid of one strand to the fourth amino acid, typically a D-alanine, of a tripeptide, tetrapeptide, pentapeptide bound to a NAM residue on a neighboring strand. In a preferred embodiment, the peptidoglycan structure is comprised of alternating NAM and NAG residues, where the majority of NAG residues are N-deacetylated, and where a tripeptide, tetrapeptide, or pentapeptide bound to the NAM residues, is crosslinked between the third amino acid of one strand to the third amino acid of a tripeptide, tetrapeptide, pentapeptide bound to a NAM residue on a neighboring strand. Thus the disclosure encompasses *C. perfringens*, and optionally *C. sordellii* and *B. subtilis* and combinations thereof, wherein a polypeptide of this disclosure has been introduced into a peptidoglycan layer of the bacteria exogenously, i.e., without being first expressed within the bacteria. The physical association between the polypeptide and peptidoglycan component can be non-covalent, and can comprise, for example, the polypeptide being adjacent to its peptidoglycan substrate such that it can perform enzymatic cleavage of the substrate, and may include cleavage intermediates, such as complexes formed between the polypeptide and the substrate during cleavage.

The polypeptide may comprise a binding portion at the carboxyl terminal side and may be characterized by an enzyme activity capable of cleaving cell wall peptidoglycan (such as an amidase activity able to act on amide bonds in the peptidoglycan) at the amino terminal side. In an embodiment, a lysin of this disclosure comprises an N-acetylmuramoyl-L-alanine amidase.

The disclosure includes fusion proteins which comprise all, or a biologically active part, of a polypeptide according to the present disclosure linked to a heterologous polypeptide. Fusion proteins include chimeric proteins are produced, for example, by chemically combining two or more distinct proteins, or as a continuous polypeptide made by protein translation. These proteins can act independently on the same or different molecules, and hence have a potential to treat two or more different bacterial infections at the same time. These proteins may be used to treat a bacterial infection by cleaving the cell wall in more than one location, thus potentially providing more rapid or effective (or synergistic) killing from a single lysin molecule. A fusion protein can combine a lysin polypeptide with a protein or polypeptide of having a different capability, or providing an additional capability or added character to the lysin polypeptide. Chimeric and fusion proteins and polypeptides of the disclosure can be produced by standard recombinant DNA techniques.

Any of the polypeptides of this disclosure can be produced using any suitable approach, examples of which are known in the art. In certain embodiments, the polypeptides can be isolated and/or separated from a bacteriophage. In embodiments, the polypeptides are produced using any suitable expression vector, such expression vectors also being encompassed by the disclosure. Accordingly, the polypeptides may be produced by using the isolated gene encoding the lytic enzyme from the phage genome, and/or cloned versions of the gene, or any polynucleotide segment or derivative of it that encodes the polypeptides of this disclosure. The expression vector for producing a lysin polypeptide or enzyme of the invention may be suitable for expression in any suitable bacteria, including but not limited to *E. coli, Bacillus*, or any number of other suitable bacteria. The vector and/or RNA encoding it may also be used in a cell free expression system. Accordingly, all polynucleotides encoding polypeptides of this disclosure are encompassed within the invention, as are polynucleotides that hybridize, under stringent conditions, with complementary sequences of the DNA sequence(s). Further variants of these sequences are contemplated for use in production of lysin enzymes according to the disclosure, including natural variants that may be obtained. Thus, a large variety of isolated nucleic acid sequences or cDNA sequences that encode phage associated lysing enzymes and partial sequences that hybridize with such gene sequences are useful for recombinant production of the lysin enzyme(s) or polypeptide(s) of the disclosure. In certain approaches a signal sequence can be included before the coding sequence. This sequence encodes a signal peptide, N-terminal to the polypeptide that communicates to the host cell to direct the polypeptide to the cell surface or secrete the polypeptide into the media, and this signal peptide is clipped off by the host cell before the protein leaves the cell.

The present disclosure also provides pharmaceutical compositions comprising the present polypeptides. Such compositions may be used prophylactically or therapeutically. The pharmaceutical compositions comprise one or more lytic polypeptide(s), and optionally include natural, truncated, chimeric or shuffled lytic enzymes, optionally combined with other components such as another polypeptide, a polynucleotide, holin protein(s), one or more antibiotics and/or as a pharmaceutically acceptable carrier, excipients, carriers or vehicles.

The present disclosure provides therapeutic compositions or pharmaceutical compositions of the lysins for use in the killing, alleviation, decolonization, prophylaxis or treatment of the Gram-positive bacteria described herein, including bacterial infections or related conditions. The present disclosure provides therapeutic compositions or pharmaceutical compositions of the lysins of the invention for use in treating, reducing or controlling contamination and/or infections by Gram-positive bacteria, particularly including *C. perfringens*. Compositions are thereby contemplated and provided for therapeutic applications and local or systemic administration. Additionally, different lytic polypeptide(s) genetically coded for by different phage for treatment of the same bacteria may be used. These lytic enzymes may also be any combination of naturally occurring lytic enzymes, truncated lytic polypeptide(s), variant lytic polypeptide(s), and chimeric and shuffled lytic enzymes. The lytic enzyme(s)/polypeptide(s) in a therapeutic or pharmaceutical composition for Gram-positive bacteria may be used alone or in combination with antibiotics or, if there are other invasive bacterial organisms to be treated, in combination with other phage associated lytic enzymes specific for other bacteria being targeted. Various antibiotics may be optionally included in the therapeutic composition with the enzyme(s) or polypeptide(s). The pharmaceutical composition can also include a one or more of a pharmaceutically acceptable carrier or diluent. More than one lytic enzyme or polypeptide may be included in the therapeutic composition. Additionally, compositions of this disclosure may further comprise other enzymes and/or mucolytic peptides, such as lysostaphin.

Compositions of this disclosure may further include at least one additional agent which can also potentiate the bactericidal activity of the composition. Antimicrobials act largely by interfering with the structure or function of a bacterial cell by inhibition of cell wall synthesis, inhibition of cell-membrane function and/or inhibition of metabolic functions, including protein and DNA synthesis. Antibiotics can be subgrouped broadly into those affecting cell wall peptidoglycan biosynthesis and those affecting DNA or protein synthesis in Gram-positive bacteria. Cell wall synthesis inhibitors, including penicillin and antibiotics like it, disrupt the rigid outer cell wall so that the relatively unsupported cell swells and eventually ruptures. Antibiotics affecting cell wall peptidoglycan biosynthesis include glycopeptides, which inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin. Penicillins act by inhibiting the formation of peptidoglycan cross-links. The functional group of penicillins, the β-lactam moiety, binds and inhibits D,D-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin. Polypeptides interfere with the dephosphorylation of the C55-isoprenyl pyrophosphate, a molecule that carries peptidoglycan building-blocks outside of the plasma membrane. A cell wall-impacting polypeptide is bacitracin.

If the compositions include an antibiotic any suitable antibiotic can be added, such as erythromycin, clarithromycin, azithromycin, roxithromycin, other members of the macrolide family, penicillins, cephalosporins, and any combinations thereof in amounts which are effective to enhance (including but not limited to synergistic enhancement) the therapeutic effect of the lytic enzyme. Virtually any other antibiotic may be used with the lytic enzymes of this disclosure. Therapeutic or pharmaceutical compositions may comprise lytic polypeptide(s) combined with a variety of carriers to treat the illnesses caused by the susceptible bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as ethylenediaminetetracetic acid disodium salt (EDTA); sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$), and others. Glycerin or glycerol (1,2,3-propanetriol) is commercially available for pharmaceutical use. It may be diluted in sterile water for injection, or sodium chloride injection, or other pharmaceutically acceptable aqueous injection fluid. The polypeptides may be provided in an environment having a controlled pH, which allows for activity of the lytic enzyme/polypeptide(s). For example if a human or a non-human animal has been exposed to another human or non-human animal with mucosal infection, the lytic enzyme/polypeptide(s) will reside in the mucosal lining and prevent and/or inhibit colonization of the infecting bacteria. Prior to, or at the time the altered lytic enzyme is put in the carrier system or oral delivery mode, the polypeptide may be provided in a stabilizing buffer environment for maintaining a pH range between about 4.0 and about 9.0, more preferably between about 5.5 and about 8.5.

A stabilizing buffer may allow for the optimum activity of the polypeptide(s). The buffer may contain a reducing reagent, such as dithiothreitol. The stabilizing buffer may also be or include a metal chelating reagent, such as EDTA, or it may also contain a phosphate or citrate-phosphate buffer, or any other buffer. A mild surfactant can be included in a therapeutic or pharmaceutical composition in an amount effective to potentiate the therapeutic effect of the lytic enzyme/polypeptide(s) may be used in a composition. Suitable mild surfactants include esters of polyoxyethylenesorbitan and fatty acids (Tween series), octylphenoxypolyethoxy ethanol (Triton-X series), n-Octyl-β-D-glucopyranoside, n-Octyl-β-D-thioglucopyranoside, n-Decyl-β-D-glucopyranoside, n-Dodecyl-β-D-glucopyranoside, and biologically occurring surfactants, e.g., fatty acids, glycerides, monoglycerides, deoxycholate and esters of deoxycholate.

Preservatives may also be used in this invention and may, for example, comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidinedigluconate, or a combination thereof.

In embodiments a therapeutically effective amount of a lytic enzyme is used. Therapeutically effective amount means that amount of a polypeptide of this disclosure that will elicit the biological or medical response of a subject that is being sought by a health care provider, regardless of whether for human or veterinarian purposes. In particular, with regard to Gram-positive bacterial infections and growth of Gram-positive bacteria, the term "effective amount" is intended to include an effective amount of a polypeptide of this disclosure that will bring about a biologically meaningful decrease in the amount of or extent of infection of Gram-positive bacteria, including having a bactericidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity. Such changes can be compared to changes in any suitable reference, such as a value determined by exposure of a similar amount to bacteria. Suitable controls and control values to determine, for example, relative killing activity, will be apparent to those skilled in the art given the benefit of the present disclosure.

Effective amounts of polypeptides of this disclosure will depend in part on whether the lytic enzyme/polypeptide(s) will be used therapeutically or prophylactically, the duration of exposure of the recipient to the infectious bacteria, the size and weight of the individual, etc. The duration for use of the composition containing the enzyme/polypeptide(s) also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day.

For any lytic enzyme disclosed herein, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans or non-human animals, such as for veterinary purposes. The exact dosage can be selected by the individual health care provider in view of the individual to be treated. In certain embodiments, the effective dosage rates or amounts of the polypeptide(s) to be administered, and the duration of treatment will depend in part on the seriousness of the infection, the weight of the patient, the duration of exposure of the recipient to the infectious bacteria, and a variety of a number of other variables. The composition may be administered anywhere from once to several times a day, and may be administered for a short or long term period. The usage may last for days or weeks. Any dosage form employed should provide for a minimum number of units for a minimum amount of time. The concentration of the active units or milligrams or micrograms of enzymes believed to provide for an effective amount or dosage of enzymes may be selected as appropriate. The amount of active units per mL (or micrograms/kilogram body weight) and the duration of time of exposure depend on the nature of infection, and other factors that will be evident to those skilled in the art given the benefit of this disclosure. In particular, dosage forms employed should provide for a minimum number of units for a minimum amount of time. The concentration of the active units of enzyme believed to provide for an effective amount or dosage of enzyme may be in the range of any of the aforementioned weight/kg of body weight, and/or may comprise a suitable amount of enzymatic activity units/unit of volume.

The present invention encompasses antibacterial methods, including methods for killing of Gram-positive bacteria, for reducing a population of Gram-positive bacteria, for treating or alleviating a bacterial infection, for treating a human subject exposed to pathogenic bacteria, and for treating a human subject at risk for such exposure. In certain embodiments, a composition of this disclosure is administered to an individual in need thereof. The individual can be a human individual for example, who is diagnosed with, suspected of having, or is at risk for contracting a bacterial infection. In other embodiments, the invention includes such approaches for use with non-human animals, including but not limited to avian animals and mammals. In embodiments, the individual is a domesticated bird kept by humans for their eggs, their meat or their feathers (e.g., poultry). These birds are typically members of the superorder Galloanserae (fowl). Birds that can be treated using compositions of the invention thus include but are not limited to chickens, turkeys and ducks. In other embodiments, the non-human mammal is a companion animal, such as a feline or canine, guinea pigs, mice, or rabbits, or is livestock, including but not limited to bovine livestock. In embodiments, the disclosure includes administering separate compositions comprising a lytic enzyme of this disclosure to a population of animals. In embodiments, the population of animal comprises a population of bacteria that are in physical association with a polypeptide of this disclosure.

In embodiments, the disclosure pertains to prophylaxis and/or therapy of an infection by any of *C. perfringens, C.*

*sordellii*, or *C. histolyticum* that is correlated with or is causative of any of food poisoning, gastrointestinal infections not associated with food, necrotic enteritis, bacteremia, sepsis, toxic shock syndrome, gas gangrene, massive edema, pneumonia, endocarditis, arthritis, peritonitis, myonecrosis, or a gynecologic infection, or an infection of the umbilical stump in newborns.

Methods of using the therapeutic composition comprising a lytic enzyme/polypeptide(s) include administration by any acceptable approaches including but not limited to topically, orally and parenterally. For example, the polypeptide(s) can be administered intramuscularly, intrathecally, subdermally, subcutaneously, intravenously, or by aerosol to treat infections by Gram-positive bacteria. In embodiments, the disclosure comprises direct application of the polypeptide(s) using any suitable approaches to directly bring the polypeptide in contact with the site of infection or bacterial colonization, such as to the gastrointestinal tract, mucosa, application to a wound, application to the vaginal canal, expression by probiotics, and such.

Compositions for treating infections or contaminations comprise an effective amount of at least one lytic enzyme according to the invention, and may further comprise a carrier for delivering at least one lytic enzyme to the infected or contaminated skin, coat, or internal gastrointestinal surface of an individual.

For compositions requiring absorption in the stomach and upper small intestine and/or topical delivery to these sites, particularly compositions with narrow absorption windows, bioadhesive, and/or gastroretentive drug delivery systems can be effective. Compositions requiring absorption or topical delivery only in the small intestine, enteric-coated, bioadhesive drug delivery systems can be utilized. For compositions requiring absorption or topical delivery only in the lower small intestine and colon enteric-coated, bioadhesive drug delivery systems can be utilized. Pharmaceutical compositions of the invention may be, but are not limited to solutions, dispersions, emulsions, powders, pellets, beads, granules, tablets, compacts, sustained release formulations, capsules, microcapsules, tablets in capsules, tablets in tablets, microspheres, shear form particles, floss, and flakes or mixtures thereof. Tablets include single layered tablets, multilayered tablets, mini tablets, bioadhesive tablets, caplets, matrix tablets, tablet within a tablet, mucoadhesive tablets. Sustained release formulations include but are not limited to matrix type controlled release, membrane diffusion controlled release, site targeted, osmotically controlled release, pH dependent delayed release, timed release, pulsatile release, hydrodynamic balanced system; powders, pellets, beads, granules for suspension.

Compositions comprising polypeptides of this disclosure can be directed to the mucosal lining, where, in residence, they kill colonizing disease bacteria. The mucosal lining includes, for example, the upper and lower respiratory tract, eye, buccal cavity, nose, rectum, vagina, periodontal pocket, intestines and colon. For birds, the compositions can be formulated for use on the skin and/or feather follicles.

Due to natural eliminating or cleansing mechanisms of mucosal tissues, conventional dosage forms may not be retained at the application site for any significant length of time. It may thus be advantageous to have materials, which exhibit adhesion to mucosal tissues, to be administered with one or more polypeptides and other complementary agents over a period of time. The disclosure therefore includes use of mucoadhesives, including but not necessarily limited sustained release mucoadhesive and/or bioadhesive formulations, which are known in the art.

Infections may also be treated by injecting into the infected tissue a therapeutic agent comprising the appropriate lytic enzyme(s)/polypeptide(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diaminetetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein. Other phage associated lytic enzymes, along with a holin protein, may be included in the composition.

In an embodiment the disclosure comprises an article of manufacture that comprises at least one container, the container having within it a polypeptide of this disclosure which is optionally present in a pharmaceutical formulation, the container optionally included printed material having an indication that the polypeptide and/or the pharmaceutical formulation comprising it is for treating and/or preventing an infection by Gram-positive bacteria, which may be indicated to be *Clostridium perfringens*, and which may further include an indication that the composition is used for veterinary purposes, such as for treating a bacterial infection in avian animals. In embodiments, the avian animals are Anseriformes or Galliformes, and include but are not limited to any type of waterfowl. In embodiments, the avian animals are Galliformes and thus include any members of the order of heavy-bodied ground-feeding birds that includes turkey, grouse, chicken, New World quail and Old World quail, ptarmigan, partridge, pheasant, junglefowl and the Cracidae. In embodiments, the avian animals are domesticated fowl, including but not limited to domesticated chickens and turkeys. In embodiments, the chickens are roosters or hens. In embodiments, the chickens are *Gallus gallus*, such as *Gallus gallus domesticus*. In embodiments, the avian animals are adults, or juveniles. In embodiments, the avian animals are broiler chickens. In embodiments, a composition of this disclosure is administered to a population of avian animals, i.e., a flock. In embodiments, from 50-100% members of the flock receive the composition.

In embodiments, compositions of this disclosure can be used for detecting bacteria. In embodiments, the whole PlyCP025, or a segment of it can be used for diagnostic approaches. In embodiments, the segment comprises the binding domain or the catalytic domain of PlyCP025. Variations in the amino acid sequences as described above are included in connection with diagnostic approaches. In certain approaches such polypeptides are reversibly or irreversibly attached to a substrate. The polypeptides that have been reversibly or irreversibly attached to a substrate may be in physical association with any bacteria as further described herein. The substrate may be a component of a diagnostic device. Compositions comprising antibodies bound to polypeptides are also included within the scope of this disclosure. In certain approaches the PlyCP025 polypeptides described herein are components in an immunological assay, such as for use as a capture or detection agent in, for example, an ELISA assay. In certain approaches the PlyCP025 polypeptides are detectably labeled. Any detectable label can be used, non-limiting examples of which include fluorescent labels, labels that can be detected via colorimetric assays, and polypeptides that can produce a detectable signal, such as Green Fluorescent Protein, or any other protein that produces a detectable signal. In embodiments, PlyCP025 polypeptides described herein are used in various diagnostic approaches to determine the presence, absence, type and/or amount of bacteria, including but not necessarily limited to any one or any combination of *C. perfringens, C. sordelli* and *C. histolyticum*. Such approaches comprise contacting a sample with one or more PlyCP025 polypeptides described herein such that a complex between a PlyCP025 polypeptide and targeted bacteria (if present) is formed, and detecting the PlyCP025 polypeptide that is bound to the bacteria. Any biological sample can be used. Suitable samples include but are not necessarily limited to tissues and biological fluids. In embodiments, the sample comprises blood, urine, saliva, lacrimal secretions, mucosa, esophageal fluid, feathers, skin or skin cells, or any combination thereof. The sample can be obtained using any suitable technique and implement, such as a needle or a swab. The sample can be used directly or can be subjected to a processing step prior to being analyzed. In embodiments, determining a value for binding of one or more PlyCP025 polypeptides to bacteria in a sample can be performed, and if desired can be compared to any suitable control to determine the presence, absence, amount and/or type of bacteria in the sample.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

This Example describes the materials and methods used to produce the results, which are described in the subsequent examples.

Bacterial Strains and Growth Conditions

*Clostridium perfringens* strains ATCC 13124 (type A), ATCC 3626 (type B), ATCC 27324 (type B), ATCC 3631 (type C), ATCC 51880 (type D), *Clostridium difficile* ATCC 43255 and *Clostridium histolyticum* ATCC 8034 were obtained from ATCC. Two recent clinical isolates of *Clostridium perfringens* were also used. *Clostridium histolyticum, Clostridium septicum* (ATCC 12464), *Clostridium bifermentans* (ATCC 638), and *Clostridium sordellii* (ATCC 9714) were purchased from Microbiologics. *Streptococcus pyogenes* D471, *Pseudomonas aeruginosa* RS1, *Bacillus subtilis* SL4, *Bacillus anthracis* 1659 and ΔSterne, *Bacillus thuringiensis* 766, and *Staphylococcus aureus* RN4220 belong to the Rockefeller University collection. The methicillin-susceptible *S. aureus* (MRSA) was also used. All strains were stored at −80° C. and cultivated at 37° C. *Staphylococcus, Streptococcus, Pseudomonas*, and *Bacillus* strains were cultivated in Difco brain heart infusion (BHI) broth (Spectrum). *Escherichia coli* was grown in Luria-Bertani (LB) broth (BD Biosciences). *Clostridium* strains were cultured in BHIS medium (BHI supplemented with yeast extract [0.5%, wt/vol] and L-cysteine [10%, wt/vol]) and incubated in a Whitley A35 anaerobic chamber (Microbiology International, MD) supplied with an anaerobic gas mixture (10% CO2, 85% N2, 5% H2) (T.W. Smith).

Subcloning of the *C. perfringens* PlyCP025cat

The nucleotide sequence of PlyCP025 gene was acquired from the NCBI database (WP_025647622.1). The protein sequence it encodes is given above as SEQ ID NO:1. The nucleotide sequence was synthesized, and inserted into a pUC57 vector after codon optimization for *E. coli* expression (GenScript, NJ). After product verification by sequencing, the catalytic domain of PlyCP025, namely, PlyCP025-cat (SEQ ID NO:2 given above), was generated by inserting a stop codon at the end of the amino acid sequence of the catalytic domain, Gly175, using a primer set 5'-GCCGCCGAATTCATTATGAGCAAAATCTTTGGTCTGGATGC (SEQ ID NO:3) and 3'-CGCCTGCAGTTAGCCGATGGTTTTGTCCAGCAGACCTTCGG (SEQ ID NO:4, listed in the 5' to 3' direction). The construct was transformed into NEB 5-α F'Iq competent *E. coli* using EcoRI and PstI restrictive enzymes (New England BioLabs). Positive clones were identified by colony PCR and sent for DNA sequencing (Genewiz, NJ).

The Expression and Purification of Recombinant PlyCP025 and its Catalytic Domain After nucleotide sequence verification, the aforementioned clones were propagated in LB broth containing 100 μg/ml ampicillin to mid-log phase. The culture was then induced with 0.2% arabinose at 30° C. overnight. Cells were then pelleted, resuspended in 20 mM phosphate buffer (pH 7.0) containing EDTA-free complete Mini protease inhibitor cocktail (Roche), and lysed with an EmulsiFlex C-5 homogenizer (Avestin, Ottawa, Canada). Lysate debris was removed via ultracentrifugation at 4° C. (32,000×g, 45 min), and the supernatant was sterile filtered through a 0.2-μm filter. The target protein was then purified from the supernatant with a HiTrap cation-exchange column (GE Healthcare, Uppsala, Sweden). Lysin was eluted using a stepwise gradient of 0.0 to 1.0 M NaCl in 50 mM phosphate buffer (PB) (pH 7.0). Extra salt was removed by filtration with a 10-kDa-cutoff Ultra Centricon (Amicon).

Lytic Activity Assays

*C. perfringens* ATCC13124 strain was grown to mid-log phase under anaerobic conditions, and cells were harvested by centrifugation (3,000×g, 5 min). Pellets were washed twice and resuspended in PB to generate a final optical density at 600 nm (OD600) of approximately 0.9. The lytic activity of lysin was calculated based on reduction in OD600 as measured in 96-well plates using a SpectraMax Plus reader (Molecular Devices, Sunnyvale, Calif.). For each sample, 20 μl of lysin (50 μg/ml final concentration) or an equal volume of 20 mM PB was added to 180 μl of cell resuspension. The drop in OD600 at 37° C. was measured once per minute for 60 min.

To study the effect of pH on the activity of lysin, the same experimental conditions and optical drop assays described above were performed with buffers of different pH, i.e., 20 mM PB (pH 6.0, 7.0, and 8.0). To study the effect of salt and cation concentrations on the activity of lysin, PB (pH 8.0) that contained various concentrations of NaCl (50 mM, 100 mM, 200 mM or 400 mM) was used. All experiments were performed in duplicates.

CFU Reduction Assay

*C. perfringens* ATCC13124 strain was grown to mid-log phase under anaerobic conditions, and cells were harvested by centrifugation (3,000×g, 5 min). The pellet was washed twice and resuspended in PB to a final concentration of $10^8$ cfu/ml. For each sample, 20 μl of lysin (50 μg/ml final concentration) or an equal volume of 20 mM PB was added to 180 μl of cell resuspension for lytic reaction. Every 15 minutes, 50 μl was sampled from the reaction and performed serial dilution in 20 mM PB. 25 μl from each serial dilution was then plated onto BHI agar plate. After overnight incubation in the anaerobic condition, the number of colony at each time point was counted from the dilution that contains 20-40 colonies. The final bacterial titer was calculated based on a summation of the dilution fold and the colony count.

Example 2

Figure 1:
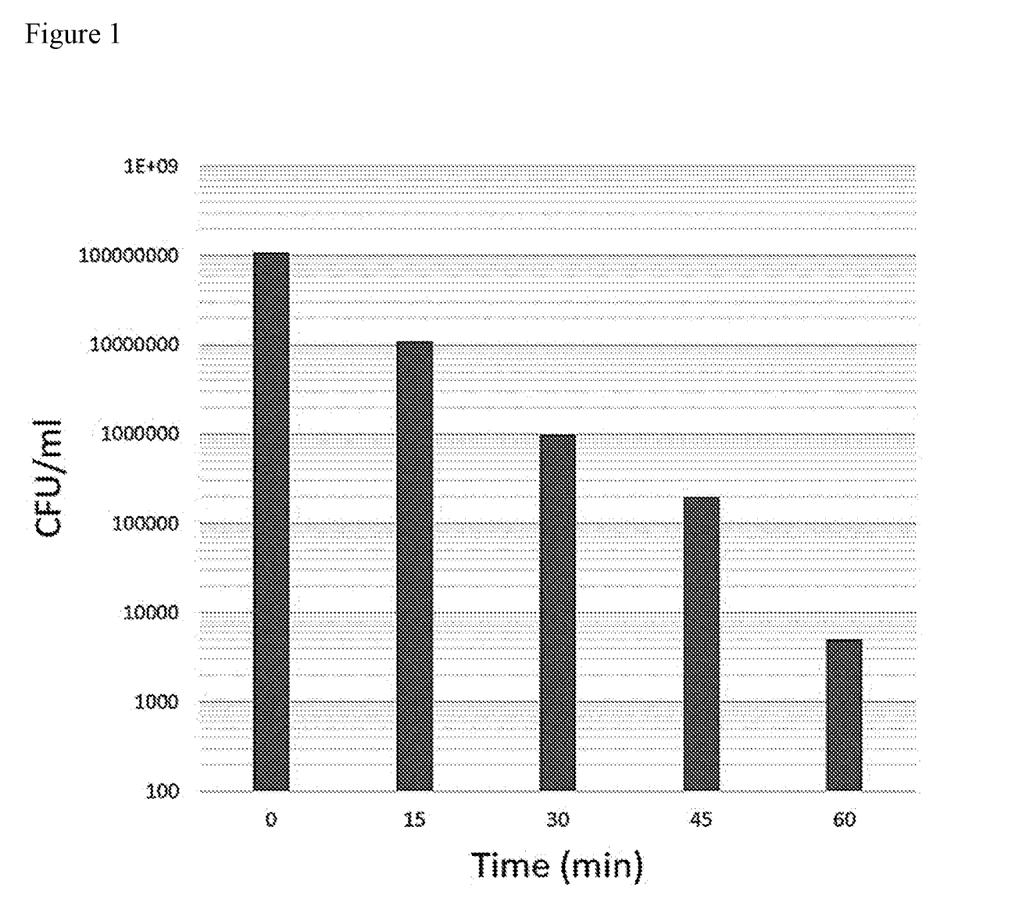
FIG. 1. The colony-forming unit (CFU) reduction of *C. perfringens* ATCC13124 by PlyCP025cat.
Figure 2A:
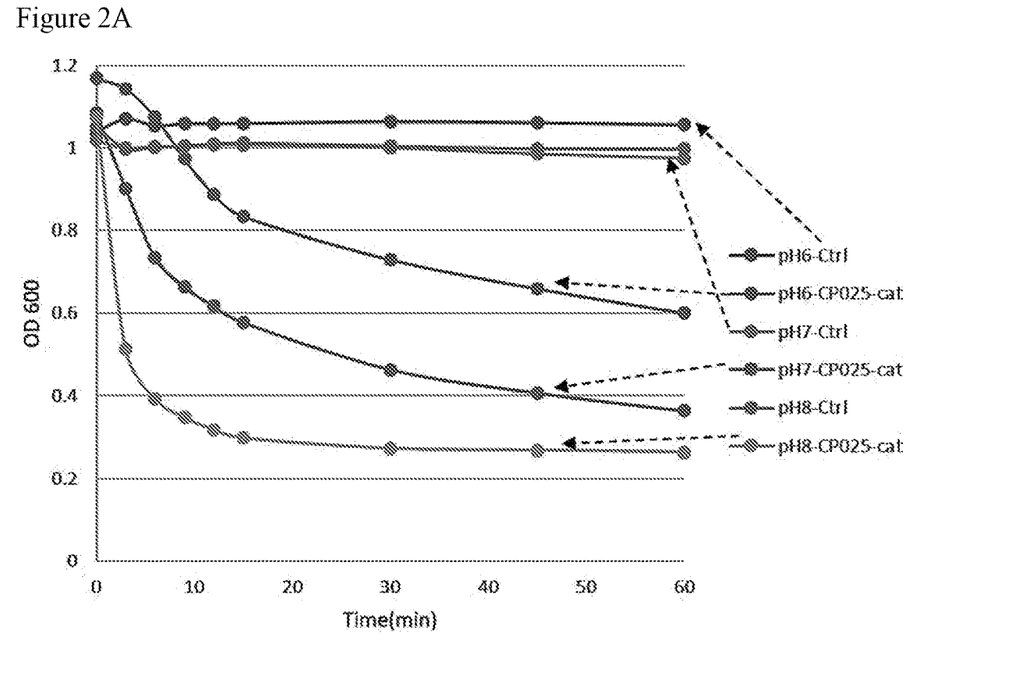
Figure 2B:
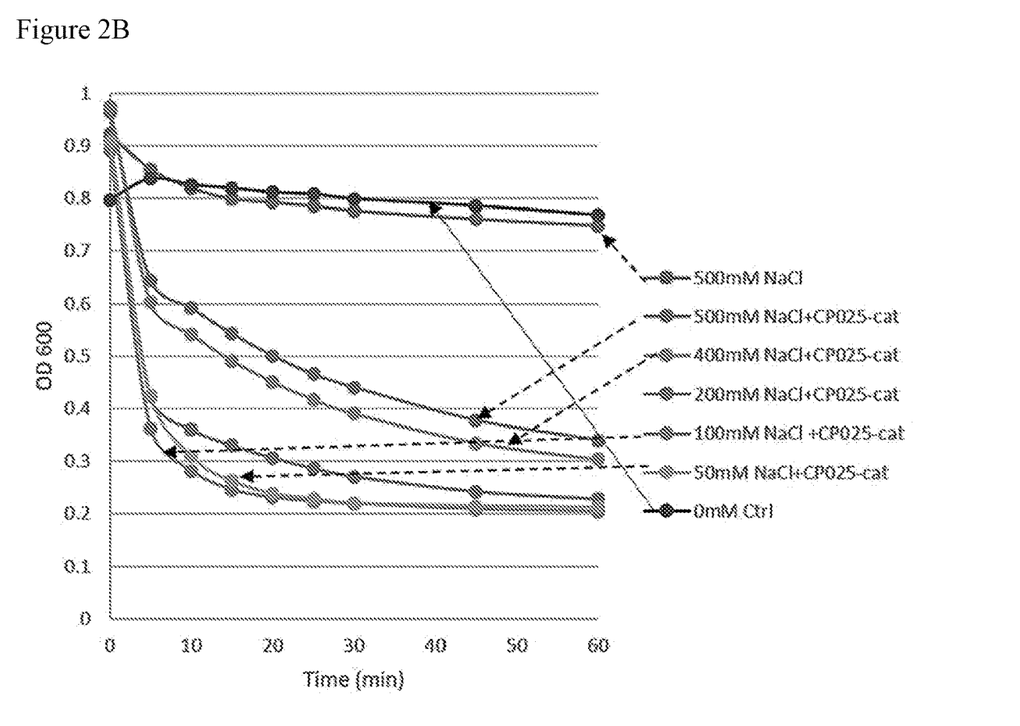
Figure 3:
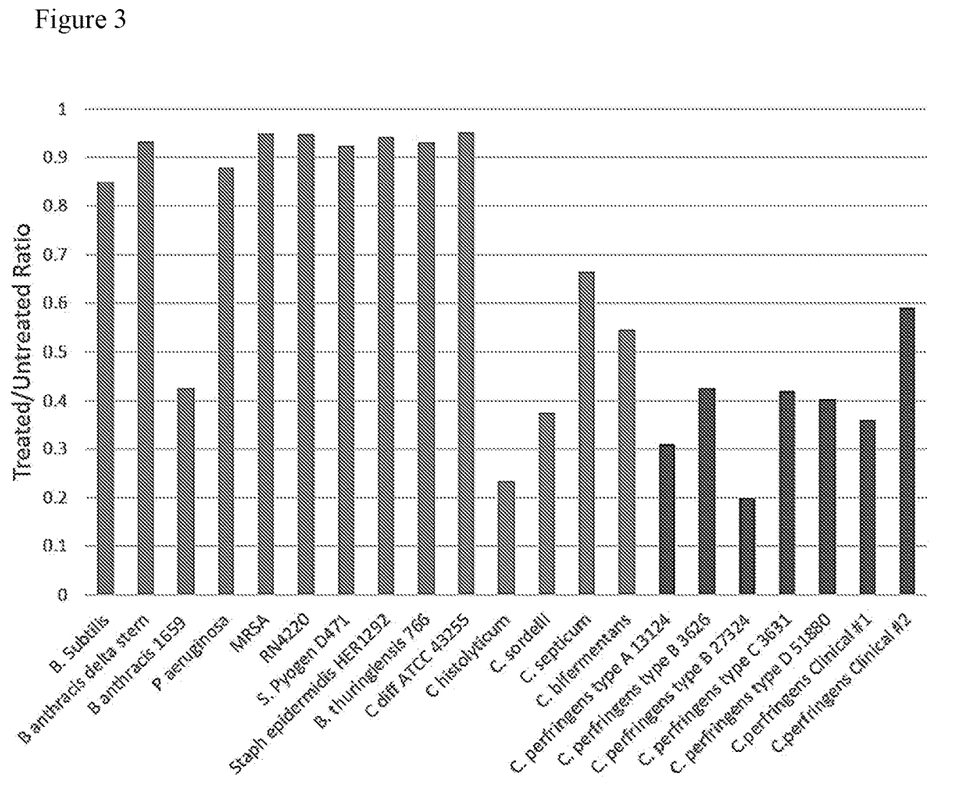
Figure 4:
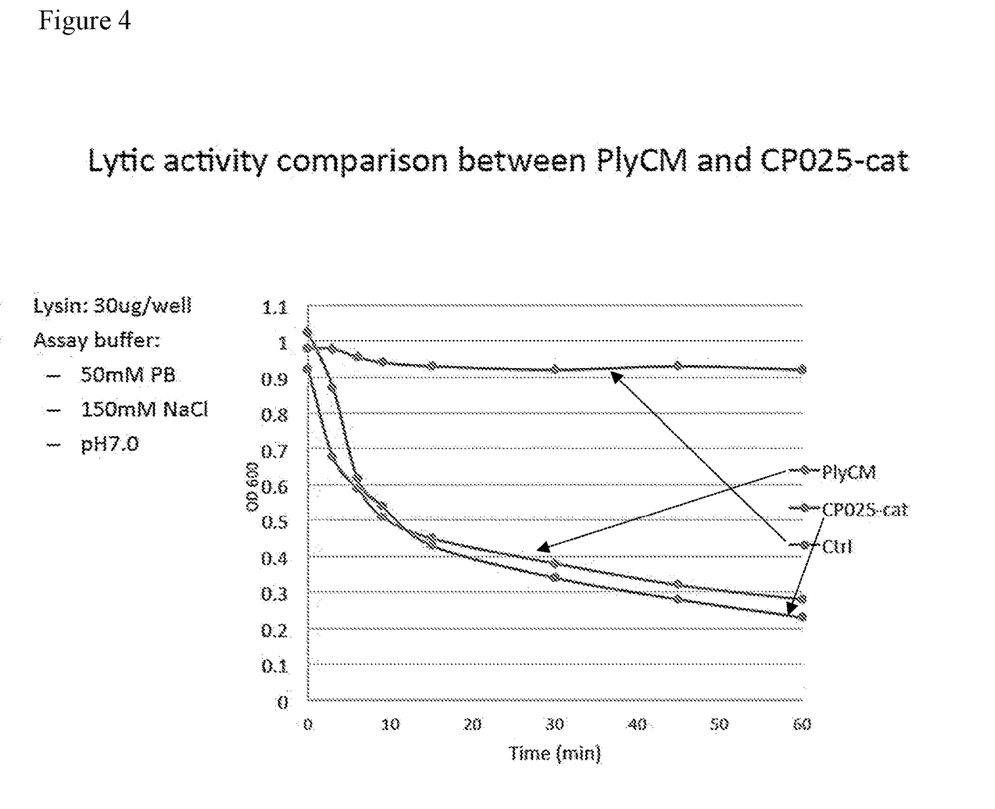

This Example describes the expression and purification of PlyCP025cat from *E. coli*. The DNA sequences of PlyCP025cat was cloned into a pBAD24 expression vector, and after arabinose induction, the whole-cell lysate was individually purified by cation-exchange chromatography. Eluted fractions that contained the purified target proteins (PlyCP025cat [19 kDa]) were pooled and run on SDS-PAGE. The final purified products were >90% pure (FIG. 1). The average yield was about 20 mg protein per liter of *E. coli* culture. These purified molecules were used in all subsequent experiments. A comparison of the activity of PlyCP025 and PlyCP025cat is shown in FIG. 4.

Example 3

This Example provides a molecular characterization of PlyCP025cat.
Lytic Activity in CFU Reduction
To measure the lytic activity of PlyCP025cat directly, a CFU reduction assay was performed. PlyCP025cat reduced the CFU of *C. perfringens* by 1 log every 15 minutes approximately (FIG. 1). In 60 min, 50 µg/ml PlyCP025cat significantly reduced the titer of *C. perfringens*, from $10^8$ to $10^4$, suggesting strong lytic activity against live *C. perfringens*.

Effects of pH and Salt

To investigate the lytic activity of PlyCP025cat under various conditions and identify the optimal activity condition, the reduction in the OD600 of *C. perfringens* suspensions was monitored over 60 min. PlyCP025cat displayed the strongest activity at pH 8.0, followed by pH7.0, and showed moderate activity at pH 6.0 (FIG. 2A).

To test salt sensitivity, the lytic activity of PlyCP025cat was measured with different NaCl concentrations. While PlyCP025cat displayed equivalent lytic activity at the end of 60 min for all concentrations tested (0 to 200 mM NaCl), greater lytic activity was observed during the initial 10 min of the reaction with minimal NaCl (FIG. 2B). At 400 mM and 500 mM NaCl, the lytic activity of PlyCP025cat was inhibited significantly.

Example 4

This Example demonstrates host specificity. To study the host specificity of PlyCP025cat, we tested its lytic activity against multiple *C. perfringens* strains, both laboratory and clinical strains, other *Clostridium* spp and several common gut flora species. All *clostridium* species were cultured anaerobically until mid-exponential phase, washed, and resuspended in 20 mM PB, pH 7.0. PlyCP025cat was then added to the bacterial suspensions at a final concentration of 50 μg/ml, and the OD600 values of each culture were recorded over 60 min. The ratio of OD600 at 60 min versus time zero was calculated. PlyCP025cat demonstrated the effective lytic activity against the majority of *C. perfringens* strains, as well as *C sordelli* and *C. histolyticum*, but displayed little to no activity against *C. septicum, C bifermentans* and *C. difficile* (FIG. 3). PlyCP025cat displayed no activity against other common gut flora species, including *B. subtillis, B anthracis* ΔSterne, *P. aeruginosa*, MRSA, *Staphylococcus aureus* RN4220, S pyogen D471, *S epidermidis* HER 1292 and *B. thuringiensis* 766. As an exception, PlyCp025cat displayed mild lytic activity against *B. anthracis* 1659 strain.

Although the present disclosure has been described with respect to one or more particular embodiments and/or examples, it will be understood that other embodiments and/or examples of the present disclosure may be made without departing from the scope of the present disclosure.

What is claimed is:

1. A method for reducing one or more of *C. perfringens, C. sordelli* or *C. histolyticum* bacteria, the method comprising contacting the bacteria with a composition comprising a lytic enzyme that comprises the amino acid sequence of SEQ ID NO:2 or an amino acid sequence with a contiguous segment having at least 95% identity to the amino acid sequence of SEQ ID NO:2 such that one or more of the one or more of the *C. perfringens, C. sordelli* or *C. histolyticum* bacteria are killed.

2. The method of claim 1, wherein the lytic enzyme consists of the sequence of SEQ ID NO:2 or an amino acid sequence with a contiguous segment having at least 95% identity to the amino acid sequence of SEQ ID NO:2.

3. The method of claim 1, wherein at least the *C. perfringens* bacteria are killed.

4. The method of claim 3, wherein the bacteria are antibiotic resistant.

5. The method claim 4, wherein at least the *C. perfringens* bacteria are antibiotic-resistant and are killed.

6. The method of claim 1, wherein the bacteria are killed are in or on a human, or in or on a non-human animal selected from avian animals and non-human mammals.

7. The method of claim 6, wherein the bacteria are in the individual in a population of bacteria that further comprise commensal gut bacterium and wherein the commensal gut bacteria are not killed by the lytic enzyme.

8. The method of claim 7, wherein the commensal bacteria are selected from *C. septicum, C. novyi, E. faecalis, E. faecium, L. rhamnosous*, and combinations thereof.

9. A method of making a recombinant polypeptide capable of killing *C. perfringens, C. sordelli* and *C. histolyticum* comprising expressing the recombinant polypeptide in a population of cells comprising an expression vector that encodes and expresses the recombinant polypeptide, wherein the recombinant polypeptide comprises an amino acid sequence of SEQ ID NO: 2 or an amino acid sequence with at least 95% identity to the amino acid sequence of SEQ ID NO:2, and separating the recombinant polypeptide from the population of cells.

10. The method of claim 9, wherein the recombinant polypeptide consists of SEQ ID NO:2 or an amino acid sequence with at least 95% identity to the amino acid sequence of SEQ ID NO:2.

11. An expression vector encoding a polypeptide of claim 9.

12. A bacterium comprising the expression vector of claim 11.

13. A method comprising contacting a sample with a polypeptide comprising the amino acid sequence of SEQ ID NO:1 or SEQ ID NO: 2 or an amino acid sequence with a contiguous segment having at least 95% similarity to SEQ ID NO:1 or SEQ ID NO: 2, and detecting binding of the polypeptide to bacteria in the sample if said bacteria that are bound to the polypeptide are present in the sample.

14. The method of claim 13, wherein the polypeptide is detectably labeled, and wherein a signal from the detectable label is detected if bacteria that are bound to the polypeptide are present in the sample.

* * * * *